United States Patent
Fujii et al.

(10) Patent No.: US 11,382,973 B2
(45) Date of Patent: Jul. 12, 2022

(54) ADJUVANT COMPOSITION AND USE THEREOF

(71) Applicant: RIKEN, Wako (JP)

(72) Inventors: Shinichiro Fujii, Wako (JP); Kanako Shimizu, Wako (JP)

(73) Assignee: RIKEN, Wako (JP)

( * ) Notice: Subject to any disclaimer, the term of this patent is extended or adjusted under 35 U.S.C. 154(b) by 124 days.

(21) Appl. No.: 16/305,630

(22) PCT Filed: Jun. 2, 2017

(86) PCT No.: PCT/JP2017/020576
§ 371 (c)(1),
(2) Date: Nov. 29, 2018

(87) PCT Pub. No.: WO2017/209274
PCT Pub. Date: Dec. 7, 2017

(65) Prior Publication Data
US 2019/0328870 A1   Oct. 31, 2019

(30) Foreign Application Priority Data

Jun. 2, 2016 (JP) .............................. JP2016-111021

(51) Int. Cl.
| | | |
|---|---|---|
| A61K 39/39 | (2006.01) | |
| A61P 37/04 | (2006.01) | |
| A61K 39/00 | (2006.01) | |
| C12N 9/64 | (2006.01) | |
| C12N 15/85 | (2006.01) | |

(52) U.S. Cl.
CPC .......... *A61K 39/39* (2013.01); *A61K 39/0011* (2013.01); *A61P 37/04* (2018.01); *C12N 9/64* (2013.01); *C12N 15/85* (2013.01)

(58) Field of Classification Search
None
See application file for complete search history.

(56) References Cited

U.S. PATENT DOCUMENTS

| | | | | |
|---|---|---|---|---|
| 6,232,456 B1 * | 5/2001 | Cohen | ................. | C12N 9/6424 435/226 |
| 7,101,977 B2 * | 9/2006 | Rosenblum | ............. | A61P 31/00 530/387.1 |
| 7,371,723 B2 * | 5/2008 | Rosenblum | ............. | A61P 19/02 424/178.1 |
| 7,691,569 B2 * | 4/2010 | Wohlgemuth | ........ | G01N 33/564 435/6.14 |
| 7,759,091 B2 * | 7/2010 | Rosenblum | ............. | A61P 43/00 435/69.1 |
| 8,043,831 B2 * | 10/2011 | Rosenblum | ............. | A61P 31/00 435/69.1 |
| 8,530,225 B2 * | 9/2013 | Rosenblum | ............. | A61P 1/04 435/252.3 |
| 9,096,840 B2 * | 8/2015 | Rosenblum | ............. | A61P 17/00 |
| 9,290,757 B2 * | 3/2016 | Madison | ................. | A61P 21/04 |
| 9,799,807 B2 * | 10/2017 | Yamada | ............... | H01L 25/0753 |
| 9,951,325 B2 * | 4/2018 | Rosenblum | ............. | C07K 16/30 |
| 10,125,359 B2 * | 11/2018 | Watson | ................... | A61P 43/00 |
| 10,323,239 B2 * | 6/2019 | Rosenblum | ............. | A61P 35/00 |
| 10,738,295 B2 * | 8/2020 | Rosenblum | .......... | C12N 9/6467 |
| 10,920,211 B2 * | 2/2021 | Rosenblum | ............... | A61P 1/18 |
| 2003/0086919 A1 | 5/2003 | Rosenblum et al. | | |
| 2004/0241646 A1 * | 12/2004 | Cohen | ................. | C12N 9/6424 435/6.18 |
| 2010/0316723 A1 * | 12/2010 | Watson | .............. | G01N 33/6872 424/489 |
| 2012/0252097 A1 * | 10/2012 | Rosenblum | ............. | A61P 35/00 435/226 |
| 2019/0256837 A1 * | 8/2019 | Rosenblum | ............. | A61P 35/02 |
| 2019/0328870 A1 * | 10/2019 | Fujii | ..................... | C07K 19/00 |
| 2020/0010821 A1 * | 1/2020 | Rosenblum | ............. | A61P 13/12 |
| 2020/0308565 A1 * | 10/2020 | Rosenblum | ............... | A61P 1/16 |

FOREIGN PATENT DOCUMENTS

| | | | | | |
|---|---|---|---|---|---|
| CA | | 3023491 A1 | * | 12/2017 | ............. A61K 39/00 |
| EP | | 3466444 A1 | * | 4/2019 | ............. C07K 19/00 |
| JP | | 2004-535202 A | | 11/2004 | |
| WO | WO-2017209274 A1 | | * | 12/2017 | ............... C12N 9/64 |

OTHER PUBLICATIONS

Liu et al., Molecular Cell, Mar. 28, 2008, 29:665-678 (Year: 2008).*
Beresford et al., Immunity, May 1999, 10:585-594 (Year: 1999).*
Ebnet et al., EMBO Journal, 1995, 14/17:4230-4239 (Year: 1995).*
Masson et al, FEBS Letters. Nov. 1986, 208/1:84-88 (Year: 1986).*
Mullbacher et al., PNAS, USA, Jun. 1996, 93:5783-5787 (Year: 1996).*
Shresta et al., Immunity, May 1999, 10:595-605 (Year: 1999).*
Burgess et al, JCB, 1990, 111:2129-2138 (Year: 1990).*
Lazar et al., Molecular and Cellular Biology, 1988, 8:1247-1252 (Year: 1988).*
Thomas E. Creighton. Proteins:Structures and Molecular Properties, 1984, pp. 314-315 (Year: 1984).*
Greenspan et al, Nature Biotechnology, 1999, 17:936-937 (Year: 1999).*
Blythe et al., Protein Science. 2005, 14:246-248 (Year: 2005).*
Houghten et al., Vaccine 86 1986,pp. 21-25 (Year: 1990).*
Bixler et al, Synthetic Vaccines, 1987, 1:39-71 (Year: 1987).*
Bowie et al, Science, 1990, 247:1306-1310 (Year: 1990).*
Kumar et al PNAS, USA, Feb. 1991, 87:1337-1341 (Year: 1991).*
Thomas E. Creighton, Protein Structure: A Practical Approach, 1989, pp. 184-186 (Year: 1989).*
Nosoh et al., Protein Stability and Stabilization through Protein Engineering, 1991, p. 197 (Year: 1991).*

(Continued)

*Primary Examiner* — Nita M. Minnifield
(74) *Attorney, Agent, or Firm* — Clark & Elbing LLP; Susan M. Michaud

(57) ABSTRACT

The present invention provides an adjuvant that can cause immune activation or particularly T cell immune activation. The present invention provides an adjuvant that can cause particularly antigen-specific immune activation or particularly T cell immune activation.

9 Claims, 6 Drawing Sheets
Specification includes a Sequence Listing.

(56) References Cited

OTHER PUBLICATIONS

Communication pursuant to Article 94(3) EPC dated Jul. 21, 2020 for European Application No. 17806824.3, Shinichiro et al., "Adjuvant Composition and Use Thereof," filed Jun. 2, 2017 (3 pages).
Yang et al., "Identification and annotation of bovine granzyme genes reveals a novel granzyme encoded within the trypsin-like locus," Immunogenetics 70(9):585-597 (2018).
Extended European Search report, dated Nov. 11, 2019 for European Patent Application No. 17806824.3, Fujii et al., "Adjuvant Composition and Use Thereof," filed Jun. 2, 2017 (6 pages).
Liu et al., "Neuroprotective Actions of PIKE-L by Inhibition of SET Proteolytic Degradation by Asparagine Endopeptidase (AEP)," available in PMC Feb. 10, 2010, published in final edited form as: Mol Cell. 29(6):665-678 (2008) (25 pages).
Andoh et al., "Granzyme A and proteinase-activated receptor 2 are involved in the induction of itch-associated responses to mosquito allergy in mice," 6th International Workshop for the Study of Itch, Sep. 4-6, Brest, France, pp. 47:638 (2011) (2 pages).
Bukczynski et al., "Costimulatory ligand 4-1 BBL (CD137L) as an efficient adjuvant for human antiviral cytotoxic T cell responses," Proc. Natl. Acad. Sci. U.S.A. 101(5):1291-1296 (2004).
Gershenfeld et al., "Cloning of a cDNA for a T cell-specific serine protease from a cytotoxic T lymphocyte," Science 232(4752):854-858 (1986).
Gherardi et al., "Macrophagic myofasciitis lesions assess long-term persistence of vaccine-derived aluminium hydroxide in muscle," Brain 124(Pt 9):1821-1831 (2001).
Hayes et al., "Induction of target cell DNA release by the cytotoxic T lymphocyte granule protease granzyme A," J. Exp. Med. 170(3):933-946 (1989).

International Search Report dated Jul. 18, 2017 for International Patent Application No. PCT/JP2017/020576, Fujii et al., "Adjuvant Composition and Use Thereof," filed Jun. 2, 2017 (6 pages).
Martina et al., "Imaging of lytic granule exocytosis in CD8+ cytotoxic T lymphocytes reveals a modified form of full fusion," Cell. Immunol. 271(2):267-279 (2011).
Martinvalet et al., "Granzyme A cleaves a mitochondrial complex I protein to initiate caspase-independent cell death," Cell 133(4): 681 -692 (2008).
Powell et al., "Examination of influenza specific T cell responses after influenza virus challenge in individuals vaccinated with MVA-NP+M1 vaccine," PLoS One 8(5):e62778 (2013) (7 pages).
Office Action dated May 7, 2021 for European Patent Application No. 17806824.3, Fujii et al., "Adjuvant Composition and Use Thereof," filed Jun. 2, 2017 (4 pages).
Grodzovski et al., "IL-2-granzyme A chimeric protein overcomes multidrug resistance (MDR) through a caspase 3-independent apoptotic pathway," Int. J. Cancer 128(8):1966-1980 (2011).
Spencer et al., "Granzyme A produced by γ9δ2 T cells induces human macrophages to inhibit growth of an intracellular pathogen," PLoS Pathog. 9(1):e 1003119, 1-8 (2013).
Kummer et al., "Localization and identification of granzymes A and B-expressing cells in normal human lymphoid tissue and peripheral blood," Clin. Exp. Immunol. 100:164-172 (1995).
Office Action dated Jan. 10, 2022, for European Patent Application No. 17806824.3, Fujii et al., "Adjuvant Composition and Use Thereof," filed Jun. 2, 2017 (3 pages).
Office Action dated May 18, 2021, for Japanese Patent Application No. 2018-521012, Shinichiro et al., "Adjuvant Composition and Use Thereof," filed Jun. 2, 2017 (with English language translation) (10 pages).

* cited by examiner

SEQUENCE LISTING

<160> NUMBER OF SEQ ID NOS: 3

<210> SEQ ID NO 1
<211> LENGTH: 913
<212> TYPE: DNA
<213> ORGANISM: Homo sapiens

```
<220> FEATURE:
<221> NAME/KEY: CDS
<222> LOCATION: (38)..(826)
<220> FEATURE:
<221> NAME/KEY: sig_peptide
<222> LOCATION: (38)..(115)

<400> SEQUENCE: 1
```

| | | | | | | | | | | | |
|---|---|---|---|---|---|---|---|---|---|---|---|
| agattttcag | gttgattgat | gtgggacagc | agccaca atg | agg | aac | tcc | tat | aga | | | 55 |
| | | | Met | Arg | Asn | Ser | Tyr | Arg | | | |
| | | | 1 | | | | 5 | | | | |

| ttt | ctg | gca | tcc | tct | ctc | tca | gtt | gtc | gtt | tct | ctc | ctg | cta | att | cct | 103 |
|---|---|---|---|---|---|---|---|---|---|---|---|---|---|---|---|---|
| Phe | Leu | Ala | Ser | Ser | Leu | Ser | Val | Val | Val | Ser | Leu | Leu | Leu | Ile | Pro | |
| | | 10 | | | | | 15 | | | | | 20 | | | | |

| gaa | gat | gtc | tgt | gaa | aaa | att | att | gga | gga | aat | gaa | gta | act | cct | cat | 151 |
|---|---|---|---|---|---|---|---|---|---|---|---|---|---|---|---|---|
| Glu | Asp | Val | Cys | Glu | Lys | Ile | Ile | Gly | Gly | Asn | Glu | Val | Thr | Pro | His | |
| | | 25 | | | | | 30 | | | | | 35 | | | | |

| tca | aga | ccc | tac | atg | gtc | cta | ctt | agt | ctt | gac | aga | aaa | acc | atc | tgt | 199 |
|---|---|---|---|---|---|---|---|---|---|---|---|---|---|---|---|---|
| Ser | Arg | Pro | Tyr | Met | Val | Leu | Leu | Ser | Leu | Asp | Arg | Lys | Thr | Ile | Cys | |
| | 40 | | | | | 45 | | | | | 50 | | | | | |

| gct | ggg | gct | ttg | att | gca | aaa | gac | tgg | gtg | ttg | act | gca | gct | cac | tgt | 247 |
|---|---|---|---|---|---|---|---|---|---|---|---|---|---|---|---|---|
| Ala | Gly | Ala | Leu | Ile | Ala | Lys | Asp | Trp | Val | Leu | Thr | Ala | Ala | His | Cys | |
| 55 | | | | | 60 | | | | | 65 | | | | | 70 | |

| aac | ttg | aac | aaa | agg | tcc | cag | gtc | att | ctt | ggg | gct | cac | tca | ata | acc | 295 |
|---|---|---|---|---|---|---|---|---|---|---|---|---|---|---|---|---|
| Asn | Leu | Asn | Lys | Arg | Ser | Gln | Val | Ile | Leu | Gly | Ala | His | Ser | Ile | Thr | |
| | | | 75 | | | | | 80 | | | | | 85 | | | |

| agg | gaa | gag | cca | aca | aaa | cag | ata | atg | ctt | gtt | aag | aaa | gag | ttt | ccc | 343 |
|---|---|---|---|---|---|---|---|---|---|---|---|---|---|---|---|---|
| Arg | Glu | Glu | Pro | Thr | Lys | Gln | Ile | Met | Leu | Val | Lys | Lys | Glu | Phe | Pro | |
| | | 90 | | | | | 95 | | | | | 100 | | | | |

| tat | cca | tgc | tat | gac | cca | gcc | aca | cgc | gaa | ggt | gac | ctt | aaa | ctt | tta | 391 |
|---|---|---|---|---|---|---|---|---|---|---|---|---|---|---|---|---|
| Tyr | Pro | Cys | Tyr | Asp | Pro | Ala | Thr | Arg | Glu | Gly | Asp | Leu | Lys | Leu | Leu | |
| | 105 | | | | | 110 | | | | | 115 | | | | | |

| cag | ctg | acg | gaa | aaa | gca | aaa | att | aac | aaa | tat | gtg | act | atc | ctt | cat | 439 |
|---|---|---|---|---|---|---|---|---|---|---|---|---|---|---|---|---|
| Gln | Leu | Thr | Glu | Lys | Ala | Lys | Ile | Asn | Lys | Tyr | Val | Thr | Ile | Leu | His | |
| | 120 | | | | | 125 | | | | | 130 | | | | | |

| cta | cct | aaa | aag | ggg | gat | gat | gtg | aaa | cca | gga | acc | atg | tgc | caa | gtt | 487 |
|---|---|---|---|---|---|---|---|---|---|---|---|---|---|---|---|---|
| Leu | Pro | Lys | Lys | Gly | Asp | Asp | Val | Lys | Pro | Gly | Thr | Met | Cys | Gln | Val | |
| 135 | | | | | 140 | | | | | 145 | | | | | 150 | |

| gca | ggg | tgg | ggc | agg | act | cac | aat | agt | gca | tct | tgg | tcc | gat | act | ctg | 535 |
|---|---|---|---|---|---|---|---|---|---|---|---|---|---|---|---|---|
| Ala | Gly | Trp | Gly | Arg | Thr | His | Asn | Ser | Ala | Ser | Trp | Ser | Asp | Thr | Leu | |
| | | | | 155 | | | | | 160 | | | | | 165 | | |

| aga | gaa | gtc | aat | atc | acc | atc | ata | gac | aga | aaa | gtc | tgc | aat | gat | cga | 583 |
|---|---|---|---|---|---|---|---|---|---|---|---|---|---|---|---|---|
| Arg | Glu | Val | Asn | Ile | Thr | Ile | Ile | Asp | Arg | Lys | Val | Cys | Asn | Asp | Arg | |
| | | | 170 | | | | | 175 | | | | | 180 | | | |

| aat | cac | tat | aat | ttt | aac | cct | gtg | att | gga | atg | aat | atg | gtt | tgt | gct | 631 |
|---|---|---|---|---|---|---|---|---|---|---|---|---|---|---|---|---|
| Asn | His | Tyr | Asn | Phe | Asn | Pro | Val | Ile | Gly | Met | Asn | Met | Val | Cys | Ala | |
| | 185 | | | | | 190 | | | | | 195 | | | | | |

| gga | agc | ctc | cga | ggt | gga | aga | gac | tcg | tgc | aat | gga | gat | tct | gga | agc | 679 |
|---|---|---|---|---|---|---|---|---|---|---|---|---|---|---|---|---|
| Gly | Ser | Leu | Arg | Gly | Gly | Arg | Asp | Ser | Cys | Asn | Gly | Asp | Ser | Gly | Ser | |
| | 200 | | | | | 205 | | | | | 210 | | | | | |

| cct | ttg | ttg | tgc | gag | ggt | gtt | ttc | cga | ggg | gtc | act | tcc | ttt | ggc | ctt | 727 |
|---|---|---|---|---|---|---|---|---|---|---|---|---|---|---|---|---|
| Pro | Leu | Leu | Cys | Glu | Gly | Val | Phe | Arg | Gly | Val | Thr | Ser | Phe | Gly | Leu | |
| 215 | | | | | 220 | | | | | 225 | | | | | 230 | |

| gaa | aat | aaa | tgc | gga | gac | cct | cgt | ggg | cct | ggt | gtc | tat | att | ctt | ctc | 775 |
|---|---|---|---|---|---|---|---|---|---|---|---|---|---|---|---|---|
| Glu | Asn | Lys | Cys | Gly | Asp | Pro | Arg | Gly | Pro | Gly | Val | Tyr | Ile | Leu | Leu | |
| | | | 235 | | | | | 240 | | | | | 245 | | | |

| tca | aag | aaa | cac | ctc | aac | tgg | ata | att | atg | act | atc | aag | gga | gca | gtt | 823 |
|---|---|---|---|---|---|---|---|---|---|---|---|---|---|---|---|---|
| Ser | Lys | Lys | His | Leu | Asn | Trp | Ile | Ile | Met | Thr | Ile | Lys | Gly | Ala | Val | |
| | | | 250 | | | | | 255 | | | | | 260 | | | |

| | | | | | |
|---|---|---|---|---|---|
| taa | ataaccgttt | cctttcattt | actgtggctt | cttaatcttt | tcacaaataa | 876 | aatcaatttg catgactgta aaaaaaaaaa aaaaaaa                                           913

<210> SEQ ID NO 2
<211> LENGTH: 262
<212> TYPE: PRT
<213> ORGANISM: Homo sapiens

<400> SEQUENCE: 2

Met Arg Asn Ser Tyr Arg Phe Leu Ala Ser Ser Leu Ser Val Val
1               5                   10                  15

Ser Leu Leu Leu Ile Pro Glu Asp Val Cys Glu Lys Ile Ile Gly Gly
                20                  25                  30

Asn Glu Val Thr Pro His Ser Arg Pro Tyr Met Val Leu Leu Ser Leu
            35                  40                  45

Asp Arg Lys Thr Ile Cys Ala Gly Ala Leu Ile Ala Lys Asp Trp Val
        50                  55                  60

Leu Thr Ala Ala His Cys Asn Leu Asn Lys Arg Ser Gln Val Ile Leu
65                  70                  75                  80

Gly Ala His Ser Ile Thr Arg Glu Glu Pro Thr Lys Gln Ile Met Leu
                85                  90                  95

Val Lys Lys Glu Phe Pro Tyr Pro Cys Tyr Asp Pro Ala Thr Arg Glu
            100                 105                 110

Gly Asp Leu Lys Leu Leu Gln Leu Thr Glu Lys Ala Lys Ile Asn Lys
        115                 120                 125

Tyr Val Thr Ile Leu His Leu Pro Lys Lys Gly Asp Asp Val Lys Pro
130                 135                 140

Gly Thr Met Cys Gln Val Ala Gly Trp Gly Arg Thr His Asn Ser Ala
145                 150                 155                 160

Ser Trp Ser Asp Thr Leu Arg Glu Val Asn Ile Thr Ile Ile Asp Arg
                165                 170                 175

Lys Val Cys Asn Asp Arg Asn His Tyr Asn Phe Asn Pro Val Ile Gly
            180                 185                 190

Met Asn Met Val Cys Ala Gly Ser Leu Arg Gly Gly Arg Asp Ser Cys
        195                 200                 205

Asn Gly Asp Ser Gly Ser Pro Leu Leu Cys Glu Gly Val Phe Arg Gly
    210                 215                 220

Val Thr Ser Phe Gly Leu Glu Asn Lys Cys Gly Asp Pro Arg Gly Pro
225                 230                 235                 240

Gly Val Tyr Ile Leu Leu Ser Lys Lys His Leu Asn Trp Ile Ile Met
                245                 250                 255

Thr Ile Lys Gly Ala Val
            260

<210> SEQ ID NO 3
<211> LENGTH: 234
<212> TYPE: PRT
<213> ORGANISM: Homo sapiens

<400> SEQUENCE: 3

Ile Ile Gly Gly Asn Glu Val Thr Pro His Ser Arg Pro Tyr Met Val
1               5                   10                  15

Leu Leu Ser Leu Asp Arg Lys Thr Ile Cys Ala Gly Ala Leu Ile Ala
                20                  25                  30

Lys Asp Trp Val Leu Thr Ala Ala His Cys Asn Leu Asn Lys Arg Ser
            35                  40                  45

Gln Val Ile Leu Gly Ala His Ser Ile Thr Arg Glu Glu Pro Thr Lys

-continued

```
    50                  55                  60

Gln Ile Met Leu Val Lys Lys Glu Phe Pro Tyr Pro Cys Tyr Asp Pro
65                  70                  75                  80

Ala Thr Arg Glu Gly Asp Leu Lys Leu Leu Gln Leu Thr Glu Lys Ala
                85                  90                  95

Lys Ile Asn Lys Tyr Val Thr Ile Leu His Leu Pro Lys Lys Gly Asp
            100                 105                 110

Asp Val Lys Pro Gly Thr Met Cys Gln Val Ala Gly Trp Gly Arg Thr
        115                 120                 125

His Asn Ser Ala Ser Trp Ser Asp Thr Leu Arg Glu Val Asn Ile Thr
    130                 135                 140

Ile Ile Asp Arg Lys Val Cys Asn Asp Arg Asn His Tyr Asn Phe Asn
145                 150                 155                 160

Pro Val Ile Gly Met Asn Met Val Cys Ala Gly Ser Leu Arg Gly Gly
                165                 170                 175

Arg Asp Ser Cys Asn Gly Asp Ser Gly Ser Pro Leu Leu Cys Glu Gly
            180                 185                 190

Val Phe Arg Gly Val Thr Ser Phe Gly Leu Glu Asn Lys Cys Gly Asp
        195                 200                 205

Pro Arg Gly Pro Gly Val Tyr Ile Leu Leu Ser Lys Lys His Leu Asn
    210                 215                 220

Trp Ile Ile Met Thr Ile Lys Gly Ala Val
225                 230
```

ADJUVANT COMPOSITION AND USE THEREOF

TECHNICAL FIELD

The present invention relates to an adjuvant that can cause immune activation, particularly T cell immune activation. The present invention particularly relates to an adjuvant that can cause antigen-specific immune activation, particularly T cell immune activation.

BACKGROUND ART

Efficiently activating the immune system and establishing antigen-specific memory is an important object in the development of vaccines for infections, cancer, and the like. For this purpose, it is necessary to use antigens and adjuvants under optimal conditions. The adjuvant is a word that is derived from "adjuvare", a Latin word meaning assistance, and refers to a substance that modifies the endogenous immunogenicity of antigens upon vaccination.

In clinic, aluminum salts (alum) such as aluminum chloride, aluminum hydroxide, and aluminum phosphate have been employed as the adjuvant and incomplete Freund's adjuvant (IFA) has been used for cancer vaccine, but the effect of these adjuvants is still not enough for inducing antigen-specific immune activation. Moreover, the mechanism of actions of these adjuvants is unclear and the problem of side effect has begun to be pointed out (Non-Patent Literature 1).

Granzyme A is a protein having the serine protease activity and was found from cytotoxic T lymphocytes (Non Patent Literature 2). The induction of apoptosis has been reported to be a function of Granzyme A (Non Patent Literature 3).

CITATION LIST

Non Patent Literature

Non Patent Literature 1: Gherardi et al., Brain, 124: 1821-1831, 2001
Non Patent Literature 2: Gershenfeld et al, Science, 232 (4752): 854-858, 1996
Non Patent Literature 3: Martinvalet et al, Cell, 133 (4): 681-692, 2008

SUMMARY OF INVENTION

Technical Problem

The present invention provides an adjuvant that can cause immune activation, particularly T cell immune activation. The present invention particularly provides an adjuvant that can cause antigen-specific immune activation, particularly T cell immune activation.

Solution to Problem

The present invention provides an adjuvant that can cause immune activation, particularly T cell immune activation. The present invention particularly provides an adjuvant that can cause antigen-specific immune activation, particularly T cell immune activation.

The present inventors have revealed that Granzyme A activates immunity independently of the serine protease activity. The present inventors have also revealed that antigen-specific immune activation occurs in this immune activation. The present inventors have further revealed that Granzyme A causes antigen-specific T cell induction, maturation of dendritic cells (for example, maturation of CD8-positive dendritic cells and/or CD8-negative dendritic cells), and the production of interferon γ. The present invention is an invention based on such findings.

Accordingly, the present invention provides the following inventions.

(1) An adjuvant composition comprising Granzyme A or a protein having an amino acid sequence having an 80% or more homology with Granzyme A.

(2) The adjuvant composition according to the aforementioned (1), wherein Granzyme A is Granzyme A whose serine protease activity is lower than that of a wild type.

(3) The adjuvant composition according to the aforementioned (2), wherein Granzyme A whose serine protease activity is lower than that of a wild type is Granzyme A in which an amino acid corresponding to an amino acid at position 184 in the amino acid sequence set forth in SEQ ID NO: 3 is changed by substitution of serine with alanine.

(4) The adjuvant composition according to any one of the aforementioned (1) to (3), for use in activating T cell immunity or B cell immunity.

(5) The adjuvant composition according to any one of the aforementioned (1) to (4), for use in maturating a dendritic cell.

(6) A composition for use in activating antigen-specific immunity, comprising an effective amount as an adjuvant of Granzyme A or a protein having an 80% or more amino acid homology with Granzyme A, and an immunogenic substance.

(7) The composition for use in activating antigen-specific immunity according to the aforementioned (6), wherein the effective amount as an adjuvant of Granzyme A or protein having an 80% or more amino acid homology with Granzyme A is comprised in the form of a conjugate with the immunogenic substance.

(8) The composition for use in activating antigen-specific immunity according to the aforementioned (6) or (7), wherein the immunogenic substance is a polypeptide and the effective amount as an adjuvant of Granzyme A or a protein having an 80% or more amino acid homology with Granzyme A is comprised in the form of a fusion protein with the immunogenic substance.

(9) The composition for use in activating antigen-specific immunity according to any one of the aforementioned (6) to (8), wherein the immunogenic substance is a tumor antigen.

(10) The composition for use in activating antigen-specific immunity according to any one of the aforementioned (6) to (9), for use as a vaccine.

(11) A composition for use in activating immunity, comprising a vector comprising a nucleic acid encoding Granzyme A or a protein having an 80% or more amino acid homology with Granzyme A.

(12) A combination of the nucleic acid as defined in the aforementioned (11) and a nucleic acid encoding a peptidic immunogenic substance, for use in activating immunity to the peptidic immunogenic substance.

(13) A composition for use in activating immunity to the peptidic immunogenic substance, wherein the combination according to the aforementioned (12) is comprised in one vector, or in two or more vectors wherein the nucleic acids are comprised separately.

(14) An animal cell transformed with the composition according to the aforementioned (13), wherein the animal cell expresses Granzyme A and the immunogenic substance.

(15) A fusion protein of a peptidic immunogenic substance and Granzyme A or a protein having an 80% or more amino acid homology with Granzyme A, the fusion protein having immunogenicity.

(16) An animal cell having the fusion protein according to the aforementioned (15).

(17) A composition for use in activating antigen-specific immunity, comprising the cell according to the aforementioned (14) or (16) as an active ingredient.

(18) A combination of an animal cell comprising Granzyme A or a protein having an 80% or more amino acid homology with Granzyme A and an immunogenic substance, for use in activating immunity to the immunogenic substance.

(19) A composition for use in activating antigen-specific immunity, comprising the combination according to the aforementioned (18).

(20) The adjuvant composition according to any one of the aforementioned (1) to (5), for use in activating immunity to the immunogenic substance, wherein the composition is administered in combination with a splenocyte incorporating an immunogenic substance.

BRIEF DESCRIPTION OF DRAWINGS

In FIG. 1, the antigen is ovalbumin. In the figure, Granzyme A may be abbreviated to grmA, and this is the same in the following figures.

FIG. 2 also illustrates that the serine protease activity of the Granzyme is hardly involved in the antigen-specific T cell induction by Granzyme A (see FIG. 2B). S184A gzmA in the figure is a mutant in which the serine protease activity of Granzyme A is substantially lost.

FIG. 5 also illustrates that administration of an antigen and Granzyme A to mice results in the production of interferon γ (see FIG. 5B). "pep" in the figure means OVA.

DETAILED DESCRIPTION OF THE INVENTIONS

Figure 1:
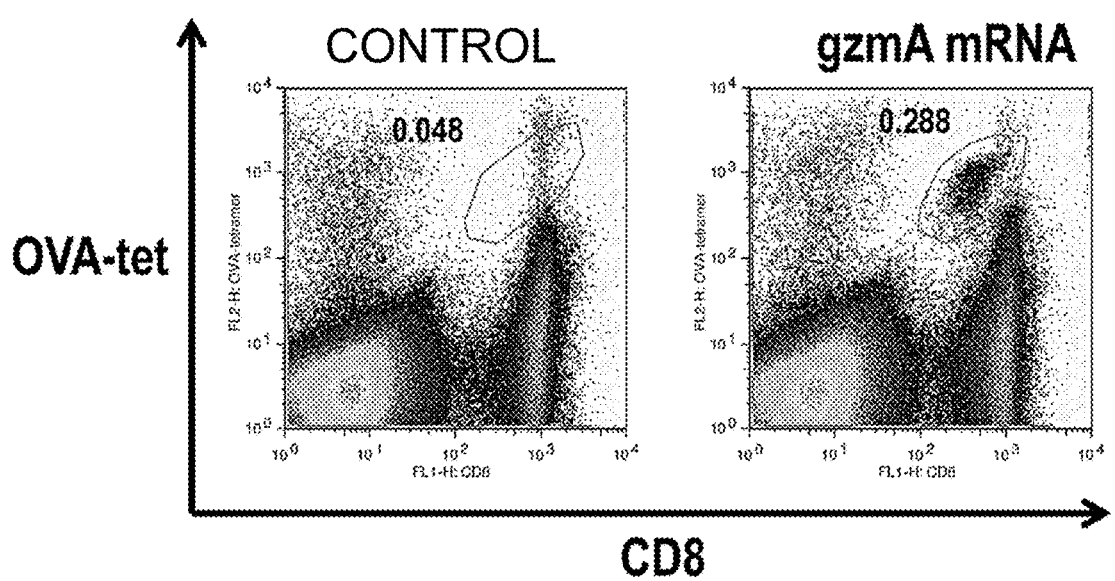
FIG. 1 illustrates that cells expressing an antigen and Granzyme A induce antigen-specific T cells.

As used herein, the "adjuvant composition" means a composition to be used as adjuvant. For example, when the adjuvant composition is administered in combination with an immunogenic substance simultaneously or separately, the adjuvant composition can activate immunity to the immunogenic substance. As used herein, the adjuvant composition may be referred to as the immune activation agent, the immunoenhancer, or the composition for use in activating immunity. As used herein, the adjuvant composition may be used for various purposes, such as for use in inducing antigen-specific T cells, in particular, for use in inducing antigen-specific CD8 single positive cells, and for use in maturing dendritic cells (for example, CD8-positive dendritic cells and CD8-negative dendritic cells). The term "CD8 single positive cells" means T cells that are positive for CD8 and negative for CD4 and examples thereof include cytotoxic T lymphocytes (CTL).

As used herein, the "immunogenic substance" means a substance having immunogenicity in general. Examples of the immunogenic substance include substances that serve as an exogenous antigen in the subject to which the substance is administered (for example, toxoids such as bacterial toxoids, viruses, virus-like particles (VLPs), protein complexes, proteins, polypeptides, liposome, antigen-presenting cells, cells presenting an antigen peptide of interest, and immune-stimulating complexes and fragments thereof) and substances that serve as an endogenous antigen in the subject to which the substance is administered (for example, tumor antigens such as MART-1/Melan-A, Mage-1, Mage-3, gp100, tyrosinase, CEA, PSA, CA-125, erb-2, Muc-1, Muc-2, TAG-72, AES, FBP, C-lectin, NY-ESO-1, galectin-4/NY-00-27, Pec60, HER-2/erbB-2/neu, telomerases, G250, Hsp105, point mutant ras oncogene, point mutant p53 oncogene, carcinoembryonic antigen, proteinase 3, WT-1, hTERT, PRAME, PML/RAR-a, DEK/CAN, cyclophilin B, TEL-MAL1, BCR-ABL, OFA-iLRP, Survivin, Sperm protein 17, SPAN-Xb, CT-27, MUC1, and fragments thereof). As used herein, the "peptidic immunogenic substance" means a peptide having modification such as posttranslational modification or a peptide which having no modification such as posttranslational modification, wherein the peptide has immunogenicity.

As used herein, the "nucleic acid" means a biopolymer in which nucleotides are linked. Examples of the nucleic acid include deoxyribonucleic acid (DNA) and ribonucleic acid (RNA).

As used herein, the "animal" means an animal having an immune system, in particular, acquired immunity and examples thereof include vertebrates, for example, birds or mammals, for example, mammals, for example, primates, in particular, human. As used herein, the term animal is used in the meaning including human as described above and animals excluding human are described as nonhuman animals.

As used herein, "administering A and B in combination" or similar expressions mean that, as long as A and B are administered in combination, A and B may be administered in mixture or A and B may be administered in separate preparations simultaneously or sequentially.

As used herein, "Granzyme A" is a serine protease produced by cytotoxic T lymphocytes (CTL) and natural killer cells (NK cells) and also referred to as cytotoxic T-lymphocyte-associated serine esterase 3 (CTLA3), cytotoxic T lymphocyte and natural killer cell-specific trypsin-like serine protease, or HANUKAH factor serine protease (HFSP). Examples of human Granzyme A include a protein encoded by mRNA deposited under NM_006144.3. The protein (having the amino acid sequence set forth in SEQ ID NO: 2) encoded by mRNA deposited under NM_006144.3 is produced as Granzyme A precursor having a 26 amino acids of signal peptide at the N-terminus and amino acids at positions 29 to 254 in SEQ ID NO: 2 serve as a matured Granzyme A. The amino acid sequence of the matured human Granzyme A may be, for example, that set forth in SEQ ID NO: 3.

In the present invention, Granzyme A has been shown to activate antigen-specific immunity. Consequently, according to the present invention, an immune activation agent or a composition for use in activating immunity including Granzyme A is provided. The immune activation was antigen-specific. Consequently, according to the present invention, an antigen-specific immune activation agent or a composition for use in activating antigen-specific immunity including Granzyme A is provided. The immune activation agent or the composition for use in activating immunity according to the present invention may be administered to a subject in combination with an immunogenic substance as an antigen or a composition including the substance. Consequently, in a certain embodiment, the immune activation agent or the composition for use in activating immunity according to the present invention may be administered to a subject in combination with an immunogenic substance as an antigen or a composition including the substance.

In the present invention, Granzyme A induced antigen-specific T cells. In the present invention, Granzyme A also induced antigen-specific T cells. In the present invention, Granzyme A further caused the maturation of dendritic cells. In particular, in the present invention, Granzyme A matured CD8-positive dendritic cells and CD8-negative dendritic cells. In particular, these antigen-specific T cell induction, antigen-specific CD8 single positive cell induction, maturation of dendritic cells, maturation of CD8-positive dendritic cells, and maturation of CD8-negative dendritic cells were induced in vivo. Consequently, according to the present invention, an antigen-specific T cell inducer, and a composition for use in inducing antigen-specific T cells, including Granzyme A; a composition for use in inducing antigen-specific CD8 single positive cells, including Granzyme A; a composition for use in maturing dendritic cells, including Granzyme A; and a composition for use in maturing CD8-positive dendritic cells and/or maturing CD8-negative dendritic cells, including Granzyme A can be provided and these may be administered, for example, to the living body. Any of these inducer and compositions may be administered to a subject in combination with an immunogenic substance as an antigen or a composition including the substance. Consequently, in a certain embodiment, the aforementioned antigen-specific T cell inducer, composition for use in inducing antigen-specific T cells including Granzyme A; composition for use in inducing antigen-specific T cells including Granzyme A; composition for use in maturing dendritic cells, including Granzyme A; and composition for use in maturing CD8-positive dendritic cells and/or maturing CD8-negative dendritic cells including Granzyme A may be an inducer or composition administered to a subject in combination with an immunogenic substance as an antigen or a composition including the substance.

In the present invention, the serine protease activity was not necessary for the adjuvant effect of Granzyme A. Consequently, in a certain embodiment, Granzyme A whose serine protease activity is lower than a wild type, for example, Granzyme A whose serine protease activity is substantially lost and Granzyme A whose serine protease activity is completely lost may be used instead of Granzyme A. Examples of Granzyme A whose serine protease activity is lower than a wild type include Granzyme A in which serine corresponding to an amino acid at position 184 in the amino acid sequence set forth in SEQ ID NO: 3 is substituted with another amino acid (for example, alanine) and such Granzyme A may be used in the present invention. Use of Granzyme A whose serine protease activity is lower than a wild type is considered to have an advantage of allowing the reduction of side effects due to the serine protease activity. Granzyme A in which serine corresponding to an amino acid at position 184 in the amino acid sequence set forth in SEQ ID NO: 3 is substituted with alanine has substantially no serine protease activity and can preferably be used in the present invention.

In the present invention, Granzyme A that serves as an active ingredient for the adjuvant effect can be used in the form of cell preparation to be supplied by cells expressing Granzyme A or cells that have incorporated Granzyme A. The cells expressing Granzyme A or the cells that have incorporated Granzyme A may be either syngeneic or allogeneic, but, from the viewpoint of allowing to supply Granzyme A without having rejection in the body of the subject to which the cells are administered, the cells are preferably syngeneic.

In other words, cells expressing Granzyme A or cells that have incorporated Granzyme A may be used instead of Granzyme A.

Consequently, according to the present invention, an immune activation agent or a composition for use in activating immunity including cells expressing Granzyme A or cells that have incorporated Granzyme A is provided. According to the present invention, an antigen-specific immune activation agent or a composition for use in activating antigen-specific immunity including cells expressing Granzyme A or cells that have incorporated Granzyme A is provided.

Moreover, according to the present invention, an antigen-specific T cell inducer, and a composition for use in inducing antigen-specific T cells, including cells expressing Granzyme A or cells that have incorporated Granzyme A; a composition for use in inducing antigen-specific T cells, including cells expressing Granzyme A or cells that have incorporated Granzyme A; a composition for use in maturing dendritic cells, including cells expressing Granzyme A or cells that have incorporated Granzyme A; a composition for use in maturing CD8-positive dendritic cells and/or maturing CD8-negative dendritic cells, including cells expressing Granzyme A or cells that have incorporated Granzyme A can be provided and these may be administered, for example, to the living body.

In the aforementioned embodiment in which Granzyme A is administered in the form of cells expressing Granzyme A or cells that incorporated Granzyme A, the immunogenic substance may be incorporated by the cells with Granzyme A or may be expressed by the cells.

Moreover, in this embodiment, Granzyme A may be administered to the subject in combination with an immunogenic substance as an antigen or a composition including the substance or cells having the substance. In a certain embodiment, the immune activation agent or the composition for use in activating immunity according to the present invention may be a composition administered to a subject in combination with an immunogenic substance as an antigen or a composition including the substance. Upon administration, the immunogenic substance may be administered together with or in separate of the cells. The immunogenic substance may be administered in the form of being in the cells or on the cell membrane.

In the present invention, a protein having an amino acid sequence having an 80% or more, preferably 85% or more, more preferably 90% or more, or further preferably 95% or more sequence homology with the amino acid sequence set forth in SEQ ID NO: 3 (which may be, for example, Granzyme A having an amino acid sequence having an 80% or more, preferably 85% or more, more preferably 90% or more, or further preferably 95% or more sequence homology with the amino acid sequence set forth in SEQ ID NO: 3) may be used instead of Granzyme A. The sequence homology may be determined by, for example, the FASTA program described in Pearson and Lipman, PNAS, 85: 2444-2448, 1988 with default parameters.

In a certain aspect according to the present invention, a composition for use in activating antigen-specific immunity, comprising an immunogenic substance and an effective amount as an adjuvant of Granzyme A or Granzyme A whose serine protease activity is lower than that of a wild type or a protein having an 80% or more amino acid homology therewith is provided. Administration of the aforementioned composition according the present invention to the living body may activate immune specific for the immunogenic substance.

In a certain aspect according to the present invention, a conjugate of an immunogenic substance and Granzyme A or Granzyme A whose serine protease activity is lower than that of a wild type or a protein having an 80% or more amino acid homology therewith is provided. In the conjugate, the immunogenic substance and Granzyme A or Granzyme A whose serine protease activity is lower than that of a wild type or protein having an 80% or more amino acid homology therewith may be linked to an immunogenic substance via a linker. Such a conjugate is acceptable, unless it inhibits the adjuvant ability of Granzyme A, and may intramolecularly or intermolecularly interact to exhibit the effect as a composition for use in activating antigen-specific immunity.

In a certain embodiment, the composition for use in activating antigen-specific immunity according to the present invention may comprise an effective amount as an adjuvant of Granzyme A or Granzyme A whose serine protease activity is lower than that of a wild type or protein having an 80% or more amino acid homology therewith in the form of a conjugate with the immunogenic substance. In the certain embodiment according to the present invention, the immunogenic substance may conjugate with Granzyme A or Granzyme A whose serine protease activity is lower than a wild type or protein having an 80% or more amino acid homology therewith via a linker.

In a certain aspect according to the present invention, the immunogenic substance is a polypeptide and a fusion protein of an effective amount as an adjuvant of Granzyme A or Granzyme A whose serine protease activity is lower than that of a wild type or protein having an 80% or more amino acid homology therewith and the immunogenic substance is provided. In a certain embodiment, the immunogenic substance may be conjugated with Granzyme A or Granzyme A whose serine protease activity is lower than that of a wild type or protein having an 80% or more amino acid homology therewith via a linker. Such a conjugate may intramolecularly or intermolecularly interact to exhibit the effect as a composition for antigen-specific immune activation unless it inhibits the adjuvant ability of Granzyme A.

In a certain aspect according to the present invention, a nucleic acid encoding the fusion protein according to the present invention is provided.

In a certain embodiment according to the present invention, the immunogenic substance in the composition for antigen-specific immune activation according to the present invention is a polypeptide and the adjuvant-effective amount of Granzyme A or Granzyme A whose serine protease activity is lower than that of a wild type or protein having an 80% or more amino acid homology therewith may be comprised in the form of a fusion protein with the immunogenic substance. If the immunogenic substance is a polypeptide, then it is advantageous in that Granzyme A may be supplied as a fusion peptide. In this case, the fusion may be formed with a peptidic linker.

According to the present invention, Granzyme A and the immunogenic substance may be administered simultaneously or sequentially, in the state in which they are expressed in cells together or separately (the immunogenic substance may be a membrane protein and in such a case, presented on the cell surface or VLP) or taken up by cells. The cells may have Granzyme A and the immunogenic substance as a conjugate as described above or may have Granzyme A and a peptidic immunogenic substance as a fusion protein as described above. Here, "cells have X" means that the cells may include X or may display X on the cell surface.

In this embodiment, animal cells may be self cells or non-self cells to the subject to which the cells to be administered and the non-self cells may be, for example, allogenic animal cells. The kind of the cells is not particularly limited, but may be, for example, somatic cells, dendritic cells, hemocytes, lymphocytes, splenocytes, or the like.

Methods for expressing a protein such as the Granzyme in cells are well-known to those skilled in the art and examples of the methods that can be used include use of a virus vector, use of an expression plasmid vector, introduction of mRNA, and the like.

Methods for making cells take up a protein such as Granzyme and an immunogenic substance are well-known to those skilled in the art and a person skilled in the art can perform such a method as appropriate. For example, in the present invention, cells may be made take the immunogenic substance up by using splenocytes as cells and incubating the cells under hyperosmotic conditions in the presence of the immunogenic substance and then inducing apoptosis under hypo-osmotic conditions (see, for example, Iyoda et al., J. Exp. Med., 195 (10): 1289-1302).

In certain embodiment according to the present invention, the immunogenic substance may be a tumor antigen.

In a certain embodiment according to the present invention, all adjuvant compositions and compositions for antigen-specific immune activation according to the present invention may be administered to vertebrates, for example, birds or mammals, for example, mammals, for example, primates, in particular, human.

The composition for antigen-specific immune activation according to the present invention may be used as vaccine. For example, the composition for antigen-specific immune activation according to the present invention may be used as vaccine such as cancer vaccine and vaccine against infection for the purpose of treatment or prevention. When used as vaccine for the purpose of treatment, the composition for antigen-specific immune activation according to the present invention is administered to a subject in need thereof, for example, a subject having cancer or infection or a subject diagnosed to have cancer or infection. When used as vaccine for the purpose of the prevention, the composition for antigen-specific immune activation according to the present invention is administered to a subject in need thereof, a subject suspected to have cancer or infection or a subject diagnosed to be suspected to have cancer or infection, a subject for which the prevention of recurrence of cancer is desirable or a subject diagnosed to be one for which the prevention of recurrence of cancer is desirable, or a subject desired to be prevented from having infection or a subject diagnosed to be prevented from having infection is desirable. Consequently, according to the present invention, a composition for antigen-specific immune activation comprising Granzyme A or Granzyme A whose serine protease activity is lower than that of a wild type or a protein having an 80% or more amino acid homology therewith for use as a vaccine, for example, for use as a vaccine such as a cancer vaccine or a vaccine against an infection is provided. In the cancer vaccine, the immunogenic substance may be a tumor antigen and the tumor antigen may be included in the immunogenic composition in a variety of forms including the form presented on cells or the form presented on VLP. Moreover, in the vaccine against infection, the immunogenic substance is preferably a vaccine used for the prevention of infection.

In the present invention, a combination (in particular, an unnatural combination) of a nucleic acid encoding Granzyme A or Granzyme A whose serine protease activity is lower than that of a wild type or a protein having an 80% or more amino acid homology therewith and a nucleic acid encoding a peptidic immunogenic substance is provided. In this embodiment, the nucleic acid encoding Granzyme A or Granzyme A whose serine protease activity is lower than that of a wild type or protein having an 80% or more amino acid homology therewith and the nucleic acid encoding the peptidic immunogenic substance may be provided on the same nucleic acid or may be provided as separate nucleic acids. For example, the nucleic acid encoding Granzyme A or Granzyme A whose serine protease activity is lower than that of a wild type or protein having an 80% or more amino acid homology therewith and the nucleic acid encoding the peptidic immunogenic substance may be provided on the same vector or may be supplied on separate vectors. And when provided on the same vector, the nucleic acids may be linked in frame with or without a linker to be expressed as a fusion protein. And, for example, the nucleic acids are operably linked to the promoter that can drive the expression in the cells and can be incorporated in an expression vector(s) to enable the expression of the proteins from the nucleic acids in the cells. In the present invention, such expression vectors may also be provided. When the nucleic acid encoding Granzyme A or Granzyme A whose serine protease activity is lower than that of a wild type or protein having an 80% or more amino acid homology therewith and the nucleic acid encoding the peptidic immunogenic substance are provided on different expression vectors, the combination of the expression vectors is provided in the present invention.

In the present invention, animal cells including one or more vectors in which a combination of the nucleic acid encoding Granzyme A or Granzyme A whose serine protease activity is lower than that of a wild type or protein having an 80% or more amino acid homology therewith and the nucleic acid encoding the peptidic immunogenic substance is expressably incorporated are presented. These cells may be syngeneic or allogeneic to a subject to which the cells are administered.

According to the present invention, animal cells comprising a combination of an antigen peptide and Granzyme A or Granzyme A whose serine protease activity is lower than that of a wild type or a protein having an 80% or more amino acid homology therewith are provided. In the present invention, a composition for antigen-specific immune activation comprising animal cells comprising a combination of an antigen peptide and Granzyme A or Granzyme A whose serine protease activity is lower than that of a wild type or a protein having an 80% or more amino acid homology therewith is provided.

In the present invention, the immunogenic substance may be administered in cells in which the substance is taken up. In such a case, Granzyme A may be supplied in the same cells, or may be supplied in different cells, or may be supplied as a peptide and administered in combination with cells that have taken the immunogenic substance up. For example, in the present invention, a composition for use in activating immunity for an antigen peptide, which is administered in combination with antigen peptide uptake splenocytes and comprises Granzyme A or Granzyme A whose serine protease activity is lower than that of a wild type or a protein having an 80% or more amino acid homology therewith is provided.

In the present invention, a method for activating antigen-specific immunity in a subject, activating immunity by antigen-specific T cells (for example, CD8SP cells) and/or maturing dendritic cells, comprising administering to a subject Granzyme A or Granzyme A whose serine protease activity is lower than that of a wild type or a protein having an 80% or more amino acid homology therewith and the immunogenic substance as an antigen in combination is provided.

In the present invention, use of Granzyme A in the production of an immune activation agent or a composition for use in activating immunity is provided. In the present invention, use of Granzyme A in the production of an antigen-specific immune activation agent or a composition for use in antigen-specific immune activation is provided. In the present invention, use of Granzyme A in the production of an antigen-specific T cell inducer, a composition for use in inducing antigen-specific T cells, a composition for use in inducing antigen-specific T cells, a composition for use in maturating dendritic cells, a composition for use in maturing CD8-positive dendritic cells and/or maturing CD8-negative dendritic cells is provided.

The composition according to the present invention may include an excipient. The composition according to the present invention, for example, may be administered by parenteral administration (for example, intraperitoneal administration, intravenous administration, subcutaneous administration, intratumoral administration, or the like). The composition may be prepared to be suitable for such parenteral administration.

The composition according to the present invention may include an adjuvant other than Granzyme A. Examples of such adjuvant include, but are not limited to, aluminum hydroxide, Freund's adjuvant, and the like. Even when an adjuvant other than Granzyme A is included, the effect that induces antigen-specific T cells and/or matures dendritic cells may be provided by Granzyme A.

Proteins and peptides such as Granzyme A and the peptidic immunogenic substance may be prepared by a method well known to those skilled in the art. For example, a protein such as Granzyme A synthesized in cells by expressably introducing a nucleic acid encoding the protein such as Granzyme A into insect cells, mammal cells, or the like, may be used. Expressably inducing a protein into cells may be achieved by a method such as introducing mRNA encoding the protein into the cells or introducing a vector expressing the protein into the cells. A protein such as Granzyme A may also be synthesized, for example, by using a cell-free protein synthesis system.

An example of the expression vector that may be used is a vector that can express a protein in selected host cells. The expression vector may be an episomal vector or may be a vector that is integrated in the host cell genome when introduced in the cells. As the expression vector, vectors such as plasmid and virus vectors may be used. Such an expression vector may be designed and prepared by a method well known to those skilled in the art. In the expression vector, the target protein desired to be expressed is usually operably linked to a promoter. As the promoter, a promoter that can express a protein in host cells may be used as appropriate. The expression vector may be introduced into the cells by a method well known to those skilled in the art.

EXAMPLES

Example 1: Antigen-Specific Immune Induction

In this Example, it was revealed that Granzyme A (hereinafter, abbreviated as "gzmA") causes specific immunity to ovalbumin (hereinafter, referred to as "OVA").

mRNA (Accession number: NM_205152) encoding OVA and mRNA (Accession number: NM_006144.3) encoding Granzyme A are introduced into NIH3T3 cells by electroporation and intravenously administered to pathogen-free C57BL/6 mice from a tail vein. The spleen was extracted from mice 7 days after the administration and filtered using a cell strainer and erythrocytes were hemolyzed and washed with the ACK lysing buffer to obtain spleen-derived mononuclear cells. The obtained spleen-derived mononuclear cells were reacted with the tetramer of OVA257-264 peptide (OVA-tet, a product made by MBL Co., Ltd., product number: TS-5001-1C) and FITC-labeled anti-CD8 antibody (a product made by BioLegend, Inc., manufacturing number: 100706). The OVA-specific T cell reaction was detected with a flow cytometry. Untreated NIH3T3 cells were used as control. The result was as illustrated in FIG. 1.

As illustrated in FIG. 1, OVA-specific immune activity and in particular, CD8-positive cells were induced in the NIH3T3 cells in which Granzyme A was introduced.

Next, using mRNA of other Granzyme families (Granzyme B, K, and M) instead of Granzyme A in the description above, whether other Granzyme families have similar immune inducing activity was examined.

mRNA of OVA was introduced alone into NIH3T3 cells and the cells were intravenously administered to mice at a tail vein as described above. The relative value of the number of CD8-positive cells when mRNA of Granzyme A, Granzyme B (Accession number: NM_013542), Granzyme K (Accession number: NM_008196), or Granzyme M (Accession number: NM_008504) was introduced in addition to mRNA of OVA, relative to the number of CD8-positive cells obtained from the mice 7 days later, which is defined as 1, were compared. The result was as illustrated in FIG. 2.

Figure 2:
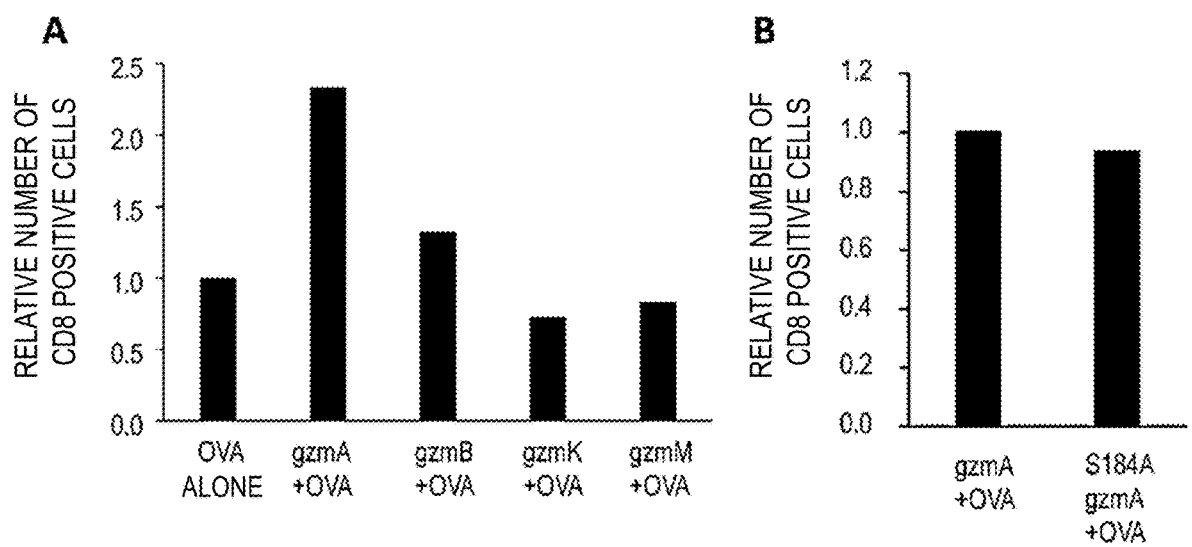
FIG. 2 illustrates that the antigen-specific T cell induction is caused more strongly by Granzyme A than by other Granzymes (see FIG. 2A).

As illustrated in the left panel in FIG. 2, Granzyme A induced OVA-specific T cells, but OVA-specific T cell induction was confirmed in neither Granzyme K nor M. In Granzyme B, a weak OVA-specific T cell induction was confirmed.

Since Granzyme A is a serine protease, whether this enzyme activity is necessary or not for the aforementioned immune activation activity that Granzyme A has was further examined. Therefore, the S184A mutant, in which serine at position 184 in the amino acid sequence of Granzyme A (the amino acid sequence set forth in SEQ ID NO: 3) is replaced with alanine, was generated and, in the experiment system described above, this mRNA was introduced with OVA mRNA into NIH3T3 cells to confirm OVA-specific T cell induction. The result was as illustrated in FIG. 2.

As illustrated in the right panel in FIG. 2, the serine protease activity was shown to be unnecessary in the immune activation activity by Granzyme A. Based on this, it is considered that side effect due to the serine protease activity can be reduced by using a mutant in which the enzyme activity of Granzyme A is inactivated, for example, when Granzyme A-introduced cells are introduced into the living body.

By this Example, it was revealed that Granzyme A can induce antigen-specific immune activation. In particular, Granzyme A induced antigen-specific T cell activation. From this, it was revealed that Granzyme A was useful as adjuvant.

Moreover, Granzyme A is considered to be expressed intracellularly in NIH3T3 cells in this Example. Since Granzyme A is not secreted from NIH3T3 cells, Granzyme A was suggested to exhibit the adjuvant effect by being released as contents of the cells, which were disrupted by immune cells in the murine body.

Example 2: Effect of Granzyme a on Maturation into Bone Marrow-Derived Dendritic Cells In the aforementioned Example, it was revealed that Granzyme A induces immune activation. In this Example, the effect of Granzyme A on the maturation into bone marrow-derived dendritic cells (hereinafter, abbreviated as "DC") was examined.

The protein of Granzyme A was synthesized according to a manufacturer manual using an insect cells (sf9 cells)-baculovirus expression system.

Murine bone marrow cells were obtained from peripheral blood of pathogen-free C57BL/6 mice. Specifically, bone marrow cells were collected from murine thighbone and neck bone and 200 ng/ml murine FLT3L (PeproTech, Inc. 250-31L) was added to induce dendritic cells in culture.

The synthesized Granzyme A (concentration: 1000 ng/mL) was added to a culture system of CD11-positive dendritic cells induced in culture and the cells were collected and washed 24 hours later. The CD86 expression intensity was examined for the maturation of dendritic cells with a flow cytometry using the anti-CD86 antibody (a product by BD Biosciences, product number: 553690) and Streptavidin-PE (ebioscience, product number 12-4317-87). As a positive control, 100 ng/ml LPS (a product made by Invivogen, product number: tlrl-eklps) was added to the culture system of CD11-positive monocytes instead of Granzyme A. Negative controls were prepared with neither Granzyme A nor LPS and with an isotype antibody instead of the anti-CD86 antibody. The result was as illustrated in FIG. 3.

Figure 3:
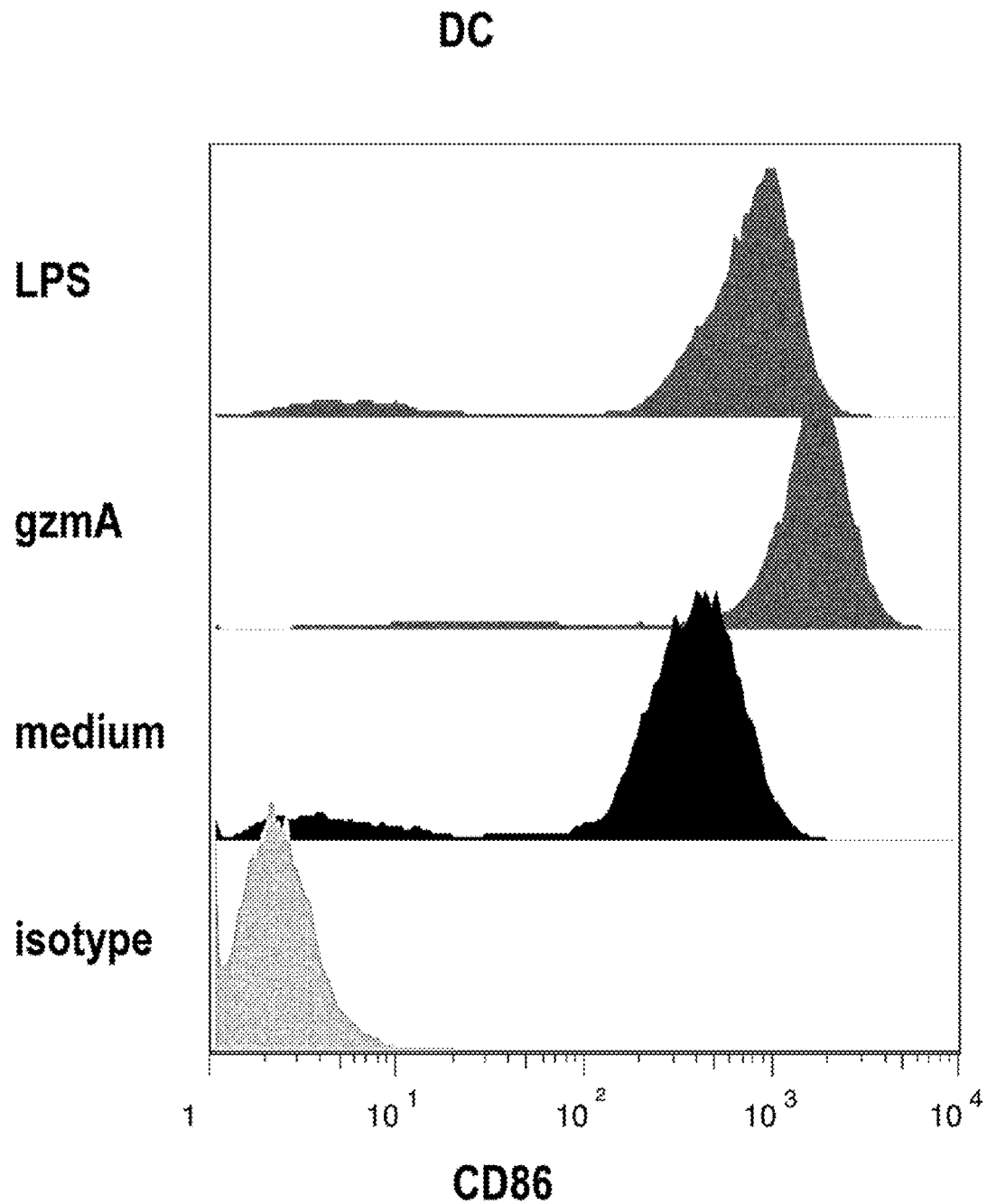
FIG. 3 illustrates that Granzyme A has an effect that matures dendritic cells as strong as or stronger than lipopolysaccharide (hereinafter, also referred to as the "LPS") does. DC in the figure means dendritic cells. CD86 in the figure is a marker for matured dendritic cells.

As illustrated in FIG. 3, the increase of CD86-positive cells was confirmed in both Granzyme A and LPS, confirming that Granzyme A matures dendritic cells as well as LPS does.

As described above, Granzyme A protein had the effect that matures bone marrow-derived dendritic cells in an in vivo system. Next, the effect of Granzyme A in vivo was confirmed.

20 μg of synthesized Granzyme A was intravenously administered to mice. The spleen was collected 16 hours after the administration and the cells were enzymatically treated with collagenase D (a product made by F. Hoffmann-La Roche Ltd, product number: 11088882001) to obtain a sufficient amount of dendritic cells. Then, the spleen dendritic cells were stained with an anti-CD11c antibody (a product of BD Biosciences, product number 550261) and an anti-CD8a antibody (a product made by BioLegend, Inc., product number: 100706) and divided into CD8-positive dendritic cells and CD8-negative dendritic cells. These cells were examined for the maturation with the intensity of CD86 expression as described above. The result was as illustrated in FIG. 4.

Figure 4:
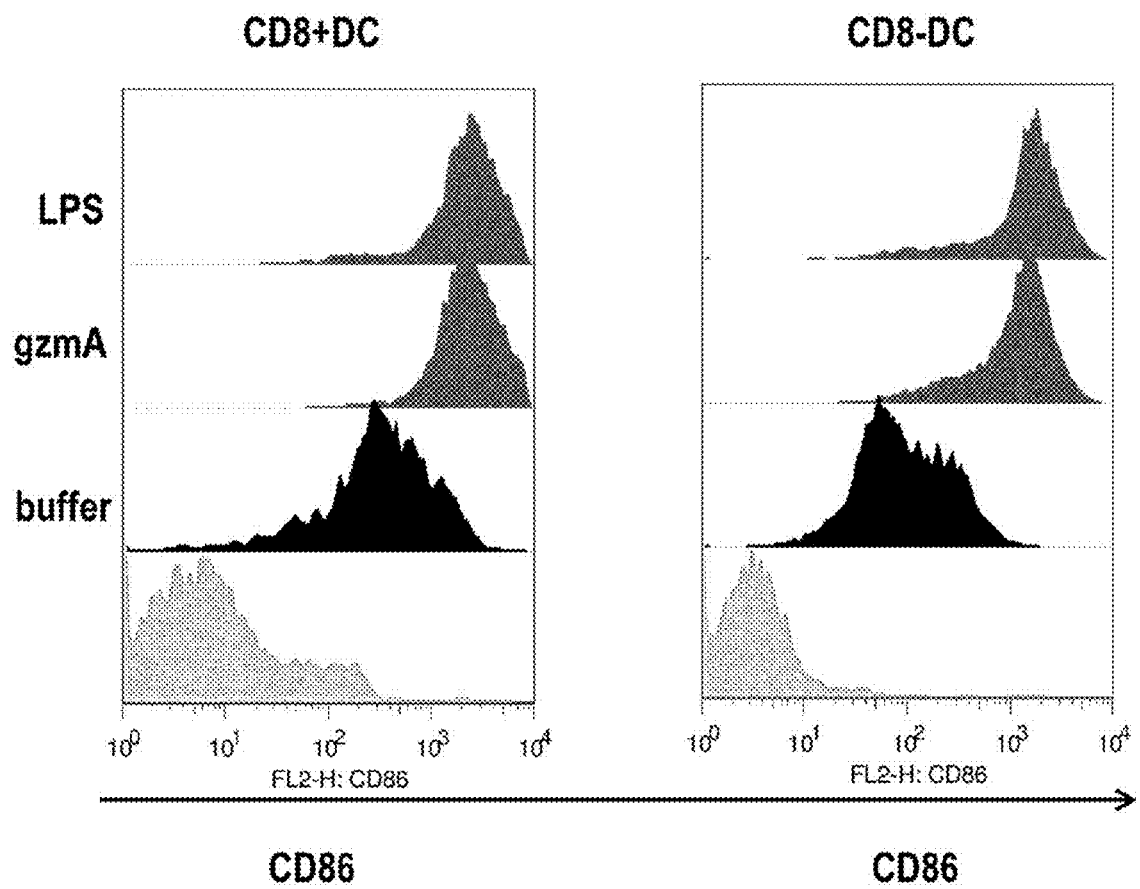
FIG. 4 illustrates that Granzyme A matures CD 8 positive dendritic cells and CD 8 negative dendritic cells as strong as or stronger than lipopolysaccharide (hereinafter, also referred to as the "LPS") does.

As illustrated in FIG. 4, both of CD8-positive dendritic cells and CD8-negative dendritic cells were confirmed in the mice that received Granzyme A as in the mice that received LPS. From this, it was found that Granzyme A has the effect that matures dendritic cells in vivo as LPS does.

Example 3: In Vivo Immune Induction with Granzyme a

In Example 1, the cells that expressed both Granzyme A and the antigen were administered to the living body. In this Example, Granzyme A was administered to the living body as a protein.

Mice were immunized with the OVA antigen and examined on the presence or absence of antigen-specific T cells according to a method described in Fujii S. et al., Journal of Experimental Medicine, 198 (2): 267-279, 2003. Specifically, splenocytes were collected from the ascitic fluid from pathogen-free C57BL/6 mice. The obtained splenocytes were incubated at 37° C. in a hyperosmotic medium (Hyper 0.5 M sucrose, 10% wt/vol polyethylene glycol 1540, 10 mM Hepes containing RPMI) in the presence of 10 mg/mL OVA antigen for 10 minutes and then in a hypo-osmotic solution (DDW plus RPMI medium) for 2 minutes to induce apoptosis and washed with PBS to prepare OVA antigen uptake splenocytes. The obtained OVA antigen uptake splenocytes were administered to mice with 20 µg of Granzyme A synthesized by a cell-free protein synthesis system and the spleen was collected to obtain spleen-derived mononuclear cells. The obtained spleen mononuclear cells were reacted with a tetramer of the OVA257-264 peptide and OVA-specific T cell response was detected with a flow cytometer. Mice that received 20 µg LPS and the OVA antigen uptake splenocytes were used as a positive control and mice received the buffer only were used as a negative control. The result was as described in FIG. 5.

Figure 5:
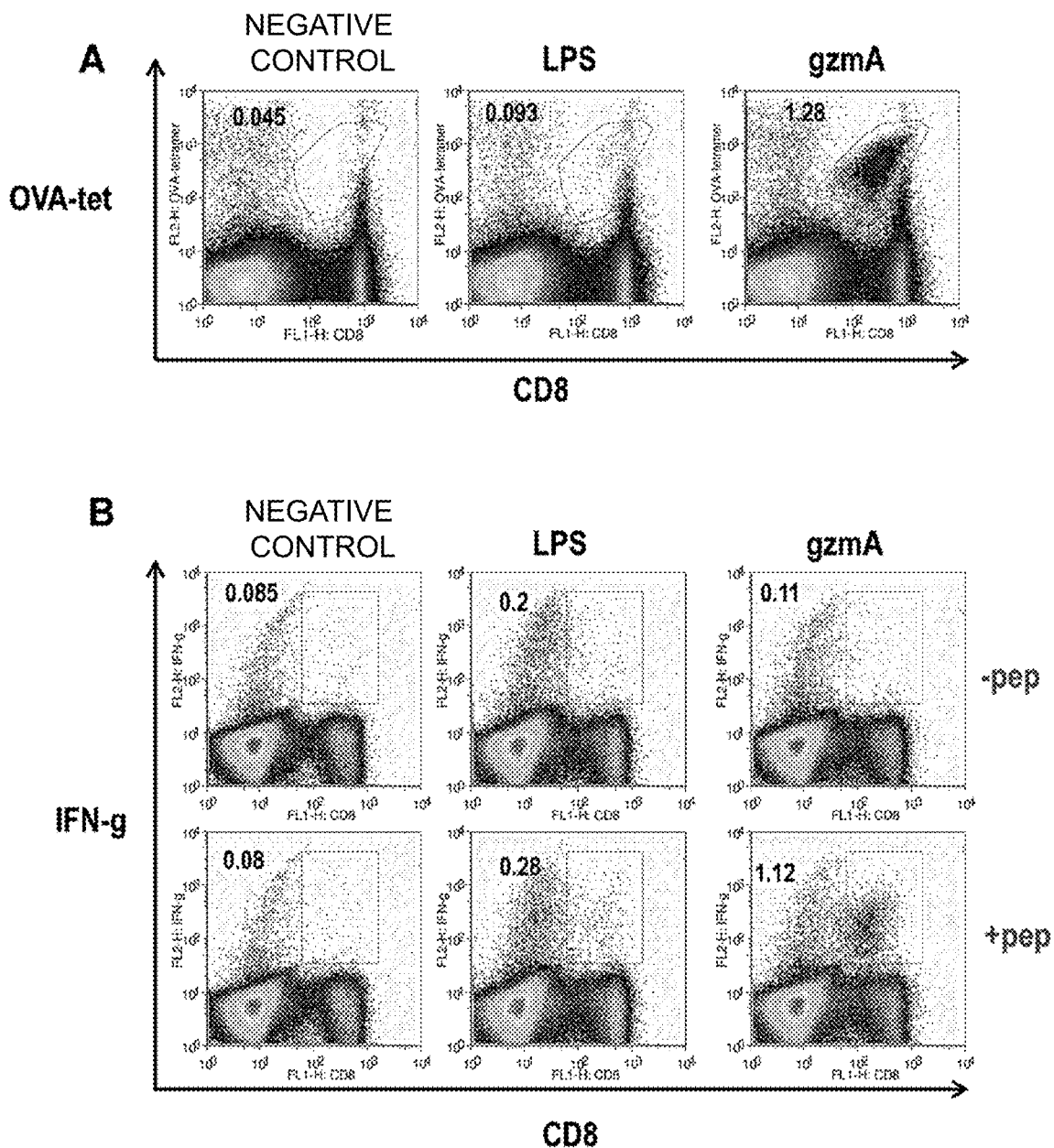
FIG. 5 illustrates that administration of an antigen and Granzyme A to mice induces antigen-specific T cells (see FIG. 5A).

As described in FIG. 5, the OVA-specific T cell induction was confirmed in the group received the OVA antigen uptake splenocytes and Granzyme A (the right panel in FIG. 5A). In contrast, the OVA-specific T cell induction was not confirmed in the group that received the OVA antigen uptake splenocytes and LPS (the middle panel in FIG. 5A).

Next, the isolated mononuclear cells were cultured in the absence or presence of the OVA peptide (at a concentration of 1 µM) for 6 hours and the change in the amount of production of interferon γ before and after the culture (T cell response) was examined. Interferon γ was measured by intracellular staining. The result was as illustrated in FIG. 5.

As illustrated in FIG. 5, it was confirmed that while the change by the stimulation of the OVA peptide was not found in the mononuclear cells obtained from the LPS administrated group, the mononuclear cells obtained from Granzyme A administrated group were stimulated with the OVA peptide to markedly produce interferon γ (FIG. 5B). This means that Granzyme A can induce the antigen-specific T cell induction and the immune response that has been difficult to induce with conventional adjuvants.

Example 4: Use as Cancer Vaccine

From the Example described above, it was revealed that Granzyme A can be utilized as the adjuvant that can induce the antigen-specific immune response. In this Example, the suppressing effect of the induced immune response on cancer cells was examined.

OVA antigen uptake splenocytes were prepared in the same way as that in Example 3. To mice, $2 \times 10^7$ OVA antigen uptake splenocytes were intravenously administered with 20 µg of Granzyme A and $1 \times 10^5$ MO4 cells were subcutaneously administered 7 days later. The proliferative effect of the MO4 cells in the body was examined. The MO4 cells are known as cells derived from the murine melanoma cell line B16 that forcibly expressed OVA. As a control, the mice to which only the MO4 cells were administered were used. The result was as illustrated in FIG. 6.

Figure 6:
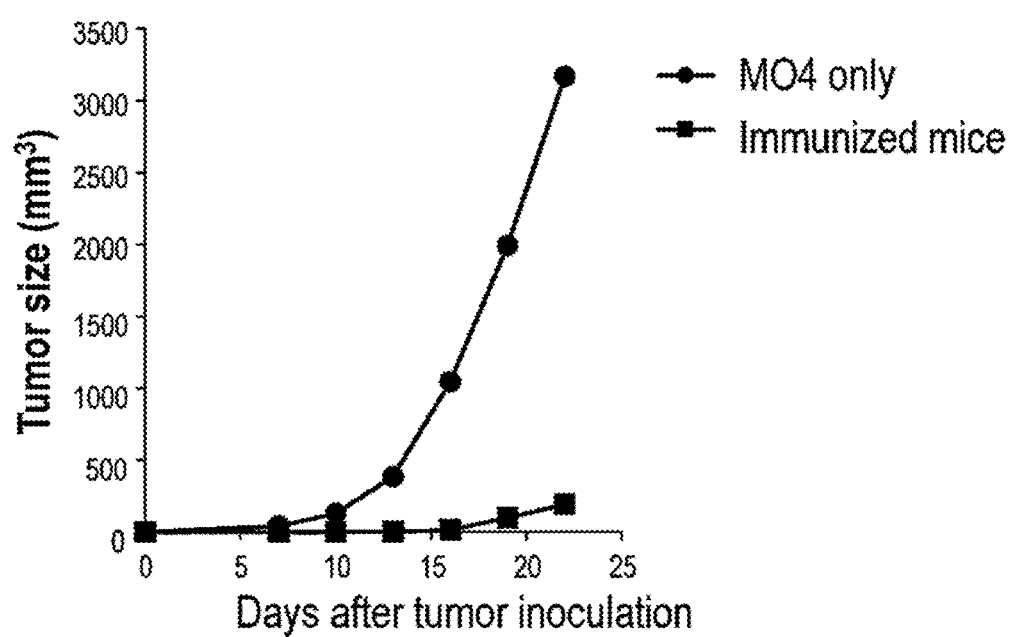
FIG. 6 illustrates that Granzyme A can suppress a cancer in an antigen-specific manner in mice.

As illustrated in FIG. 6, while the tumor size was increased rapidly in the control group without the prior administration of the OVA antigen uptake splenocytes and Granzyme A, the increase of the tumor size was markedly suppressed in the group with the prior administration. From this, Granzyme A was shown to be promising as cancer vaccine having a strong adjuvant effect.

Example 5: Analysis of Immune Response Induced by Granzyme a

In this Example, immune response induced by Granzyme A was analyzed in greater detail.

As in Example 4, 100 µl of OVA suspension (100 µg of OVA protein) and 20 µg of Granzyme A were intraperitoneally administered to mice. As a control, a system in which aluminum hydroxide (Alum) in an amount same as the OVA suspension was used as adjuvant instead of Granzyme A and a system in which only OVA antigen uptake splenocytes were administered were used.

14 days after the administration, peripheral blood was collected from the mice. The amounts of IgG1 antibody and IgG2 antibody in the collected peripheral blood were measured using a conventional method respectively. The result was as illustrated in FIG. 7.

Figure 7:
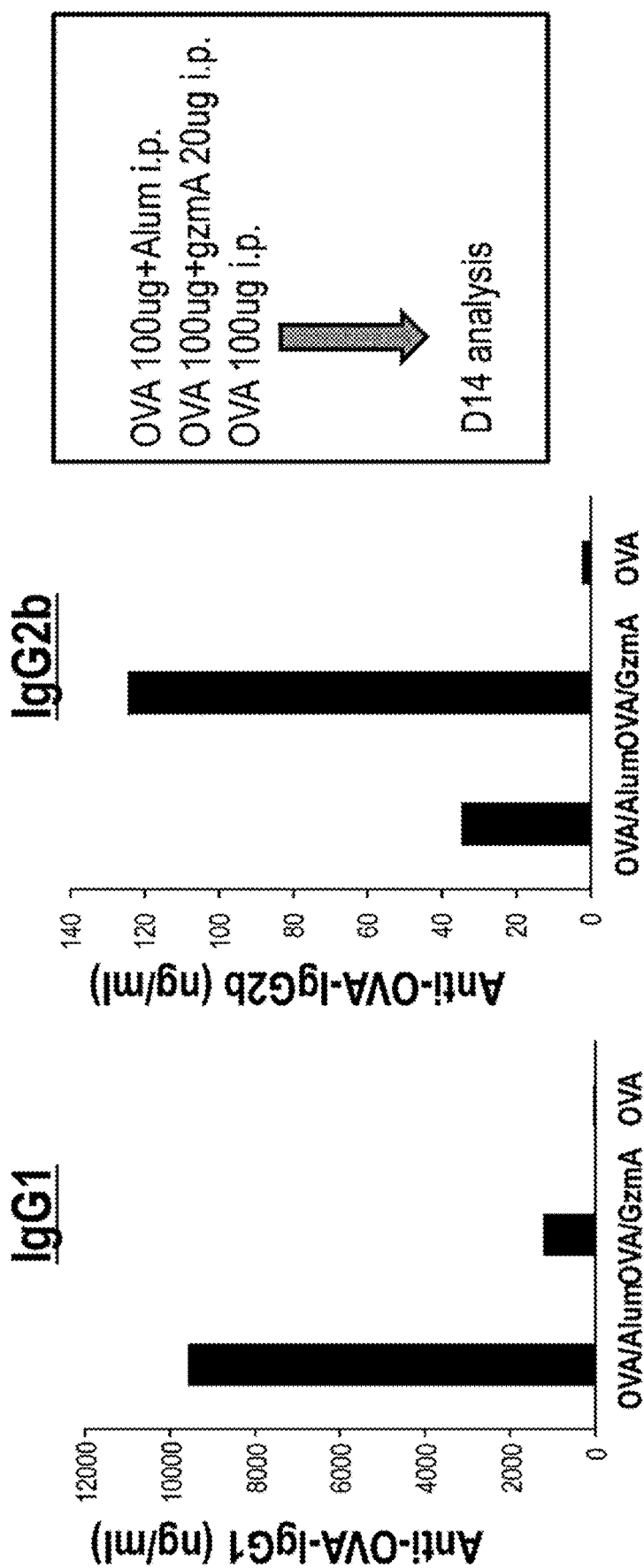
FIG. 7 illustrates that the amount of production of antigen-specific IgG2 antibody is increased in the mice to which an antigen and Granzyme A have been administered while the amount of production of antigen-specific IgG1 antibody is increased in the mice to which an antigen and aluminum hydroxide (Alum) have been administered.

As illustrated in FIG. 7, while the amount of production of the IgG1 antibody was increased when Alum was used as adjuvant, the amount of production of the IgG2 antibody was increased when Granzyme A was used as adjuvant. From this, it was revealed that Granzyme A activated the B-cell immunity as well as the T cell immunity. Moreover, it was revealed that the immune activation by Granzyme A was accomplished by a new mechanism different from that of Alum or the like.

The reduction of side effect is expected with Granzyme A since it is a biogenic protein.

The invention claimed is:

1. A method of activating antigen-specific immunity against an immunogenic substance in a subject, comprising administering to the subject an effective amount of an adjuvant composition comprising human Granzyme A and the immunogenic substance.

2. A method of activating antigen-specific immunity against an immunogenic substance in a subject, comprising administering to the subject an effective amount of an adjuvant composition comprising an immunogenic substance and Granzyme A, wherein the Granzyme A is Granzyme A in which an amino acid corresponding to an amino acid at position 184 in the amino acid sequence set forth in SEQ ID NO: 3 is changed by substitution of serine with another amino acid, and wherein serine protease activity of the Granzyme A is lower than that of a human Granzyme A having an amino acid sequence set forth in SEQ ID NO: 3.

3. The method according to claim 1, wherein human Granzyme A is administered at an effective dose for activating T cell immunity or B cell immunity.

4. The method according to claim 1, wherein human Granzyme A is administered at an effective dose for maturating a dendritic cell.

5. A method of activating antigen-specific T cell immunity or B cell immunity against an immunogenic substance in a subject, comprising administering to the subject an effective amount as an adjuvant of human Granzyme A, and the immunogenic substance.

6. The method according to claim 5, wherein the effective amount as an adjuvant of human Granzyme A is comprised in the form of a conjugate with the immunogenic substance.

7. The method according to claim 5, wherein the immunogenic substance is a polypeptide and the effective amount as an adjuvant of human Granzyme A is comprised in the form of a fusion protein with the immunogenic substance.

8. The method according to claim 5, wherein the immunogenic substance is a tumor antigen.

9. The method according to claim 1, wherein the composition is administered in combination with a splenocyte incorporating the immunogenic substance.

* * * * *